US008895708B2

(12) United States Patent
Schaap et al.

(10) Patent No.: US 8,895,708 B2
(45) Date of Patent: *Nov. 25, 2014

(54) PASTEURISATION PROCESS FOR MICROBIAL CELLS AND MICROBIAL OIL

(75) Inventors: Albert Schaap, Barendrecht (NL);
Daniel Verkoeijen, Delft (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/467,843

(22) Filed: May 9, 2012

(65) Prior Publication Data

US 2012/0316354 A1 Dec. 13, 2012

Related U.S. Application Data

(63) Continuation of application No. 12/382,103, filed on Mar. 9, 2009, now Pat. No. 8,217,151, which is a continuation of application No. 10/518,146, filed as application No. PCT/EP03/06553 on Jun. 20, 2003, now Pat. No. 7,517,953.

(30) Foreign Application Priority Data

Jun. 19, 2002 (EP) .................................... 02254262
Dec. 18, 2002 (EP) .................................... 02258713

(51) Int. Cl.
*A23J 1/00* (2006.01)

(52) U.S. Cl.
USPC .......................................... 530/412; 530/422

(58) Field of Classification Search
None
See application file for complete search history.

(56) References Cited

U.S. PATENT DOCUMENTS

| | | | |
|---|---|---|---|
| 3,106,571 A | 10/1963 | Birosel | |
| 3,958,027 A | 5/1976 | Alexander et al. | |
| 4,056,638 A | 11/1977 | Huang et al. | |
| 4,857,329 A | 8/1989 | Sako et al. | |
| 5,112,803 A | 5/1992 | Farbood et al. | |
| 5,278,325 A | 1/1994 | Strop et al. | |
| 5,340,594 A | 8/1994 | Barclay et al. | |
| 5,374,657 A | 12/1994 | Kyle | |
| 5,407,957 A | 4/1995 | Kyle et al. | |
| 5,411,872 A | 5/1995 | Rajasekaran | |
| 5,411,873 A | 5/1995 | Adams et al. | |
| 5,539,133 A | 7/1996 | Kohn et al. | |
| 6,149,949 A | 11/2000 | Coutts | |
| 6,255,505 B1 | 7/2001 | Bijl | |
| 6,391,596 B1 | 5/2002 | Talashek et al. | |
| 6,441,208 B2 | 8/2002 | Bijl et al. | |
| 8,217,151 B2 * | 7/2012 | Schaap et al. | 530/412 |
| 2005/0170479 A1 | 8/2005 | Weaver et al. | |
| 2006/0099693 A1 | 5/2006 | Kobzeff et al. | |

FOREIGN PATENT DOCUMENTS

| | | |
|---|---|---|
| DE | 19 23 259 | 12/1969 |
| DE | 1 50 627 | 9/1981 |
| EP | 0 155 420 | 9/1985 |
| EP | 0 223 960 | 9/1986 |
| EP | 0 276 541 | 9/1987 |
| EP | 0 322 227 | 6/1989 |
| EP | 0 520 624 | 12/1992 |
| EP | 0522470 | 1/1993 |
| EP | 0 568 608 | 11/1993 |
| EP | 0 611 569 | 8/1994 |
| EP | 0 957 173 | 11/1999 |
| EP | 0986960 | 3/2000 |
| EP | 1178103 | 2/2002 |
| FR | 2210662 | 7/1974 |
| FR | 2674865 | 10/1992 |
| GB | 1466853 | 3/1977 |
| JP | 64-38007 | 2/1989 |
| JP | 01038007 | 2/1989 |
| JP | 02-171127 | 7/1990 |
| JP | 05-017796 | 1/1993 |
| JP | 07-031871 | 2/1995 |
| JP | 07-188692 | 7/1995 |
| WO | 90/13656 | 11/1990 |
| WO | 91/07498 | 5/1991 |
| WO | 91/11918 | 8/1991 |
| WO | 91/14427 | 10/1991 |
| WO | 91/16443 | 10/1991 |
| WO | 92/12711 | 8/1992 |

(Continued)

OTHER PUBLICATIONS

European Search Report issued in connection with EP 10 17 4967 dated Aug. 18, 2011.
European Patent Appln. No. EP 10 17 4967, filed Mar. 21, 1997.
Li et al, "Process for Production of Arachidonic Acid Concentrate by Strain of *Mortierella alpine*", Canadian Journal of Chemical Engineering 73:135-139 (1995).
Aiba et al, Biochemical Engineering, $2^{nd}$ edition, Academic Press, pp. 253-256 (1973).
Young et al, "Process of Fats and Oils", The Lipid Handbook, $2^{nd}$ edition, Chapman & Hall pp. 249-276 (1994).
Lin et al, "Efficiency of Removing Volatiles from Menhaden Oils by Refining, Bleaching, and Deodorization", Journal of Food Science 55(6):1669-1672 (1990).

(Continued)

*Primary Examiner* — Albert Navarro
(74) *Attorney, Agent, or Firm* — Shannon McGarrah; Jacqueline Cohen; Xi Chen (57) ABSTRACT

A protocol for pasteurizing microbial cells is disclosed. The protocol has three stages, a first heating stage, a second plateau stage at which the cells are held at a (maximum and) constant temperature, and a third cooling stage. The heating and cooling stages are rapid, with the temperature of the cells passing through 40 to 80° C. in no more than 30 minutes in the heating stage. The heating rate is at least 0.5° C./minute and during cooling is at least −0.5° C./minute. The plateau maximum temperature is from 70 to 85° C. By plotting the pasteurization protocol on a time (t, minutes) versus temperature (T, ° C.) graph, a trapezium is obtained having an area less than 13,000° C. minute. This results in a smaller energy input and a better quality oil results having a peroxide value (POV) of less than 1.5 and an anisidine value (AnV) of less than 1.0.

33 Claims, 7 Drawing Sheets

(56) References Cited

FOREIGN PATENT DOCUMENTS

| WO | WO 92/13086 | 8/1992 |
|----|-------------|--------|
| WO | WO 94/28913 | 12/1994 |
| WO | WO 96/21037 | 7/1996 |
| WO | 97/37032 | 10/1997 |
| WO | WO 97/36996 | 10/1997 |
| WO | 99/65327 | 12/1999 |
| WO | WO 99/65327 | 12/1999 |
| WO | 00/15045 | 3/2000 |
| WO | 01/67886 | 9/2001 |
| WO | 02/10322 | 2/2002 |
| WO | WO 02/10423 | 2/2002 |
| WO | 03/092628 | 11/2003 |
| WO | WO 2005/063999 | 7/2005 |

OTHER PUBLICATIONS

Hempenius et al, "Preliminary Safety Assessment of an Arachidonic Acid-enriched Oil derived from *Mortierella alpine*: Summary of Toxicological Data", Food and Chemical Toxicology 35:573-581 (1997).
Jareonkitmongkol et al, "Production of an Eicosapentaenoic Acid-Containing Oil by a Δ12 Desaturase-Defective Mutant of *Mortierella alpine* 1S-4", Journal of the American Oil Chemists' Society 70(2): 119-123 (1993).
Jareonkitmongkol et al, "Production of Dihomo-γ-Linolenic Acid by a Δ5-Desaturase-Defective Mutant of *Mortierella alpina* 1S-4", 58(7):2196-2200 (1992).
Nakahara et al, "Gamma-Linolenic Acid from Genus *Mortierella*", Chapter 5, pp. 61-97 (1992).
Suzuki et al, "Studies on Production of Lipids in Fungi VIII. Influence of Cultural Conditions on Lipid Compositions of Two Strains of *Mortierella isabellina*", Yukagaku, Nihon Yukagaku Kyokai 31(11):921-931 (1982).
Shimizu et al, "Microbial Conversion of an Oil Containing α-Linolenic Acid to an Oil Containing Eicosapentaenoic Acid", JAOCS 66(3):342-347 (1989).
Database WPI, Week 199545, AN 1995-347457, XP-002603363 & JP 7 236492 (Sep. 12, 1995)—Abstract.
Database WPI, Week 198939, AN 1989-282552, XP-002603364 & J 1 207257 (Aug. 21, 1989)—Abstract.
Database WPI, Week 199009, AN 1990-063629, XP-002603365 & JP 2 026989 (Jan. 19, 1990)—Abstract.
Database WPI, Week 199545, AN 1995-347457, XP002656725 & JP 7 236492 (Sep. 12, 1995)—Abstract).
Database WPI, Week 198939, AN 1989-282552, XP002656726 & JP 1 207257 (Aug. 21, 1989)—Abstract.
Database WPI, Week 199009, AN 1990-063629, XP-002656727 & JP 2 016989 (Jan. 19, 1990)—Abstract.
El-Andaloussi et al, "Novel adenovirus-based helper system to support production of recombinant parvovirus", Cancer Care Therapy 18:240-249 (2011).
Manninen et al, "Separation of γ- and α-Linolenic Acid Containing Triacylglycerols by Capillary Supercritical Fluid Chromatography", Lipids 30(7):665-671 (1995).
Shinmen et al, "Concentration of eicosapentaenoic acid and docosahexaenoic acid in an arachidonic acid-producing fungus, *Mortierella alpina* 1S-4, grown with fish oil", Appl. Microbiol. Biotechnol. 38:301-304 (1992).
Yamada et a;. Production of Dihorno-γ-linolenic Acid, Arachidonic Acid and Eicosapentaenoic Acid by Filamentous Fungi, Chapter 7, in Industrial Application of Single Cell Oils, Kyle and Ratledge (eds), pp. 118-138 (1989).
Notice of Opposition filed Sep. 30, 2009—Patent Opposed EP 1 513 922 B1.
Reply to the Notice of Opposition filed Sep. 30, 2009 (Patent Opposed EP 1 513 922)—Reply filed May 25, 2010.
Amended Claims filed with Reply to the Notice of Opposition filed Sep. 30, 2009 (Patent Opposed EP 1 513 922)—Reply filed May 25, 2010.

Handbook of Biological Reaction Process Systems, Chapter 4—partial translation,1985 Science Forum.
Suzuki et al, Oil Chemistry 37(12):1-2 (1988)—partial translation.
Lee, Byong H., Fundamentals of Food Biotechnology, Wiley, pp. 163-165 (1996).
Jigami et al, "Comparison of lipid composition of *Candida guilliermondii* grown on glucose, ethanol and methanol as the sole carbon source", Lipids 14(11):937-42 (1979)—Abstract.
GB AN 89-201959—Abstract.
GB AN 88-341507—Abstract.
Jareonkitmongkil et al. "Production of dihomo-γ-linolenic acid by a Δ5-desaturase defective mutant of *Mortierella alpina* 1S-4" Appl. Environ. Microbiol. 58:2196-2200 (1992).
International Search Report for PCT/EP2003/006553 mailed Oct. 10, 2003.
Int'l Preliminary Examination Report for PCT/EP2003/006553 mailed Jul. 9, 2004.
DSM Submission to European Patent Office in European Patent Publication No. 1513922, Apr. 11, 2012—"Request for Postponement of Oral Proceedings".
Mewburn Ellis LLP Submission to European Patent Office in European Patent Publication No. 1513922, Apr. 3, 2012.
DSM Submission to European Patent Office in European Patent Publication No. 1513922, Apr. 3, 2012—Written submissions on behalf of patantee.
Vereenigde Submission to European Patent Office in European Patent Publication No. 1513922, Apr. 3, 2012.
DSM Submission to European Patent Office in European Patent Publication No. 1513922, Patentee's observations, Apr. 3, 2012.
Muller Fottner Steinecke Submission to European Patent Office, Third party observations in the opposition proceedings concerning European patent EP 1 513 922 B1, "Pasteurisation Process For Microbial Cells and Microbial Oil", Mar. 8, 2012.
Vereenigde Submission to European Patent Office in European Patent No. 1513922, Brief filed as an observation as defined in Art. 115 EPC, Mar. 5, 2012.
Annex, European Application No. 03 738 077.1, pp. 1-3, Jan. 4, 2012.
Summons to attend oral proceedings pursuant to Rule 115(1) EPC in European Application No./Patent No. 03738077.1-1221/1513922, Jan. 4, 2012.
Centraalbureau voor Schimmelcultures, Declaration, CBS 169.95, *Mortierella alpina*, DS30341, Jul. 25, 2011.
DSM Food Specialities, Certificate of Analysis, Material, 5574—Vevodar Oil, Batch VEVO4260/Production date Sep. 17, 2004/ Expiry Date Sep. 17, 2007 (Dec. 15, 2006).
DSM Food Specialities, Certificate of Analysis, Material, 5574—Vevodar Oil, Batch VEVO4260/Production date Sep. 17, 2004/ Expiry Date Sep. 17, 2007, Dec. 15, 2006.
Centraalbureau voor Schimmelcultures, Declaration, CBS 168.95, *Mortierella alpina*, DS30340, Jul. 25, 2011.
DSM, Report on QC data Vevodar Arachidonic acid crude oil batches, Apr. 3, 2012.
Sampling and Analysis of Commercial Fats and Oils, "p-Anisidine Value", AOCS Official Method Cd 18-90, Reapproved 1997.
In the Matter of European Patent EP 1513922 B1 of DSM IP Assets B.V. and Opposition thereto by Suntory Holdings Limited, First Declaration of Nobushige Doisaki submitted in Opposition Apr. 3, 2012.
In the Matter of European Patent EP 1513922 B1 of DSM IP Assets B.V. and Opposition thereto by Suntory Holdings Limited, Declaration of Shigeaki Fujikawa with Annexes—Submitted in Opposition Apr. 3, 2012.
E-mail to Joseph.Lenthall@mewburn.com RE:, Information about GRAS submission Notice GRN0094 (Feb. 22, 2012).
In the Matter of European Patent EP 1513922 B1 of DSM IP Assets B.V. and Opposition thereto by Suntory Holdings Limited, Second Declaration of Nobushige Doisaki submitted in Opposition Apr. 3, 2012.
In the Matter of European Patent EP 1513922 B1 of DSM IP Assets B.V. and Opposition thereto by Suntory Holdings Limited, Second Declaration of Toshiaki Nakajima submitted in Opposition Apr. 3, 2012.

(56) References Cited

OTHER PUBLICATIONS

E-mail Message from @fda.hhs.gov, Subject: FDA FOIA 2012-1959, listing of all FOIA requests received by FDA regarding Docosahexaehoic Acid, Mar. 26, 2012.

In the Matter of European Patent EP 1513922 B1 of DSM IP Assets B.V. and Opposition thereto by Suntory Holdings Limited, First Declaration of Toshiaki Nakajima with Annex submitted in Opposition Apr. 3, 2012.

ENVIRON, Letter to Linda Kahl, Ph.D. Re; GRAS Exemption Claim for Docosahexaenoic Acid Rich Oil Derived from Tuna (DHA-rich oil) and Arachidonic Acid Rich Oil Derived from *Mortierella alpina* Peyronel IS-4 (*M. alpina*) (AA-rich oil; SUNTGA40S) as Sources of DHA and AA in Term and Preterm Infant Formula, Dec. 18, 2001.

GRAS Determination For Docosahexaenoic Acid Rich Oil Derived From Tuna and Arachidonic Acid Rich Oil Derived From *Mortierella alpina*, Prepared for Ross Products Division, Abbot Laboratories, Columbus, Ohio, Prepared by ENVIRON International Corporation, Arlington, Virginia, Dec. 12, 2001.

U.S. Department of Health & Human Services, "About the GRAS Notification Program", Mar. 2009.

[Proposed Rules], From the Federal Register Online via the Government Printing Office [www.gpo.gov], [FR Doc. No: 97-9706], Federal Register 62(74):1-4 (1997).

Li et al, "Process for Production of Arachidonic Acid Concentrate by a Strain of *Mortierella alpina*", The Canadian Journal of Chemical Engineering 73:135-139 (1995).

Wyeth-Ayerst Laboratories, Letter to Office of Premarket Approval (HFS-200), Center for Food Safety and Applied Nutrition, Food and Drug Administration RE: Notice of a Chaim For Exemption From Premarket Approval, Aug. 27, 1998.

Choi Su Pak, Stability and Quality of Fish Oil During Typical Domestic Application, The United Nations University, Fisheries Training Program, pp. 1-27, Final Project 2005.

Kyle, David J., "Production and use of a single cell oil which is highly enriched in docosahexaenoic-acid", Lipid Technology, pp. 107-110, Sep. 1996.

Ministry of Agriculture, Fisheries and Food and Department of Health, ACNFP Annual Report 1996.

"VEVODAR®—A new ingredient for the fish farming industry", Nederlands, Mar. 3, 2000.

Hempenius et al, "Preliminary Safety Assessment of an Arachidonic Acid-enriched Oil derived from *Mortierella alpina*: Summary of Toxicological Data", Food and Chemical Toxicology 35:573-581 (1997).

Martek Biosciences Corporation, Letter to Dockets Management Branch (HFA-305), Food and Drug Administration Re: Feb. 9, 2000. Opinion of an Expert Panel on the Generally Recognized as Safe (GRAS) Status of ARA and DHA Single Cell Oils For Infants and Children, GRAS Panel Evaluation of DHASCO®, Martek Biosciences Corporation, Dec. 1999.

EP 1 513 922 B1 MR Main Request (mark-up), Auxiliary Request 1 (mark-up), Auxiliary Request 1-a (mark-up), Auxiliary Request 2 (mark-up), Auxiliary Request 2-a (mark-up), Auxiliary Request 3 (mark-up), Auxiliary Request 4-A (mark-up), Auxiliary Request 5-A (mark-up), Auxiliary Request 6-A (mark-up)—Submitted in Opposition on Apr. 3, 2012.

EP 1 513 922 B1 MR Main Request, Auxiliary Request 1, Auxiliary Request 1-a, Auxiliary Request 2, Auxiliary Request 2-a, Auxiliary Request 3, Auxiliary Request 4-A, Auxiliary Request 5-A, Auxiliary Request 6-A—Submitted in Opposition on Apr. 3, 2012.

Jigami et al, "Comparison of Lipid Composition of *Candida guilliermondii* Grown on Glucose, Ethanol and Methanol as the Sole Carbon Source", Lipids 14(11):937-942 (1979).

Nakahara et al, Chapter 5, pp. 61-97 of "Industrial Applications of Single Cell Oils", 1992, Ed. By Kyle & Ratledge, American Oil Chemists Society.

London GB AN 89-201959.

London GB AN 88-341507.

p. 128 of Yamada et al, Chapter 7, Production of Dihomo-γ-linolenic Acid Arachidonic Acid and Eicosapentanenoic Acid by Filamentous Fungi, Industrial Application of Single Cell Oils, Kyle & Ratledge (Eds), pp. 118-138 (1989).

Sampling and Analysis of Commercial Fats and Oils, "Peroxide Value Acetic Acid-Isoocttane Method", AOCS Official Method Cd 18-90, Reapproved 1997.

Kyle, David J., "Production and use of a single cell oil highly enriched in arachidonic acid", Lipid Technology, pp. 116-121, Sep. 1997.

* cited by examiner

PASTEURISATION PROCESS FOR MICROBIAL CELLS AND MICROBIAL OIL

This application is a continuation of U.S. application Ser. No. 12/382,103, filed Mar. 9, 2009, now U.S. Pat. No. 8,217, 151 which is a continuation of U.S. application Ser. No. 10/518,146, filed Dec. 16, 2004, now U.S. Pat. No. 7,517, 953; which is a U.S. national stage under 35 U.S.C. 371 of International Application No. PCT/EP2003/006553, filed Jun. 20, 2003, the entire contents of each of which are incorporated herein by reference.

FIELD OF THE INVENTION

The present invention relates to a process for pasteurising microbial cells, which comprises heating the cells at from 40° C. to 70° C. in no more than 30 minutes. The rate of heating during the pasteurising process can be at least 0.5° C./minute. The pasteurisation process may comprise three stages, namely a heating stage, a plateau (where the cells are held at constant temperature) and a heating stage. If one depicts the pasteurisation protocol graphically, the area under the time (minutes) versus temperature (° C.) graph is below 13,000° C. minute. After pasteurisation, a polyunsaturated fatty acid (PUFA), such as arachidonic acid, or microbial oil may be extracted from the cells. The oil may have a low peroxide value (POV) and/or low anisidine value (AnV).

INTRODUCTION

Polyunsaturated fatty acids, or PUFAs, are found naturally and a wide variety of different PUFAs are produced by different single cell organisms (algae, fungi, etc.). One particularly important PUFA is arachidonic acid (ARA) which is one of a number of Long Chain Poly-Unsaturated Fatty Acids (LC-PUFAs). Chemically, arachidonic acid is cis-5,8,11,14 eicosatetraenoic acid (20:4) and belongs to the (n-6) family of LC-PUFAs.

Arachidonic acid is a major precursor of a wide variety of biologically active compounds, known collectively as eicosanoids, a group comprising prostaglandins, thromboxanes and leukotrienes. Arachidonic acid is also one of the components of the lipid fraction of human breast milk and is thought to be essential for optimal neurological development in infants. Arachidonic acid has a wide variety of different applications including use in infant formula, foodstuffs and animal feeds.

WO-A-97/37032 (Gist-Brocades) refers to the preparation of a microbial PUFA-containing oil from pasteurised biomass. However, there is no disclosure of rapid heating to, or cooling from, a temperature at which pasteurisation takes place. Furthermore, no account is taken of the total amount of energy used during the pasteurisation process.

WO-A-00/15045 and WO-A-01/67886 both refer to the use of Mucorales fungi for use in the preparation of foodstuffs. The first of these documents refers to the need to perform RNA reduction before including the cells into foods, and suggests using a heating step. A separate pasteurisation or heat shock can be performed. The second document suggests that a heating step to reduce RNA content may be avoided by allowing the fungal cells to be kept inside the fermenter vessel, and be allowed to "ripen".

International patent application no. PCT/EP01/08902 refers to process for preparing oil mixtures by combining a crude ω6 with a crude ω3 PUFA-containing oil, to produce an oil mixture, and then purifying the crude oil mixture.

Processes involving heating biomass, or microbial cells, are known. It is also known, from WO-A-97/37032, that microbial cells can be pasteurised prior to extraction to a PIMA therefrom in the form of an oil. However, the present applicants have found that a new pasteurisation process can improve the quality of the oil that can be extracted from the pasteurised cells. In particular, the resulting oil may oxidise less, or be less oxidised, and may have a low peroxide value (POV) and/or anisidine value (AnV). In addition, the applicants have found that this new pasteurisation process is more efficient because it requires less energy. The process is therefore advantageous because not only may it improve the quality of the oil, but it may reduce costs since less energy is required.

BRIEF DESCRIPTION OF DRAWINGS

FIGS. 2 and 4 are graphs of AnV against time (hours);

DESCRIPTION OF THE INVENTION

The present invention therefore provides an improved pasteurisation process of microbial cells. Despite requiring less energy, the pasteurisation process of the invention may allow for a better quality product.

Thus, a first aspect of the present invention relates to a process for pasteurising microbial cells, the process comprising heating the cells at (a temperature comprising) from 40° C. to (60° C. or) 70° C. in no more than 30 minutes or heating the cells at a rate of at least 0.5° C./minute. This aspect therefore provides a rapid heating of the microbial cells during pasteurisation, and such a high rate of heating is not disclosed in the art. While the art gives pasteurisation temperatures, there is no appreciation or discussion of the rate of heating, or that this parameter would be important and that a relatively rapid rate can provide benefits. Indeed, high heating rates are counter-intuitive as they might be expected to cause oxidation or otherwise degrade the PUFA or oil that can be extracted from the cells.

A second aspect of the second invention relates to a process for pasteurising microbial cells, the process comprising a pasteurisation protocol that comprises (at least) three stages. These are, namely: a (first) heating stage, a (second) plateau stage (at which the microbial cells are held at a desired temperature, or where the cells are maintained at a constant and/or maximum temperature), and a (third) cooling stage. This aspect of the invention is referred to as the three-stage pasteurisation protocol. If this protocol is plotted on a graph of time versus temperature, a trapezium can result.

A third aspect of the invention relates to a process for pasteurising microbial cells, the process comprising using a pasteurisation protocol such that the area under the time (minutes) versus temperature (° C.) graph is below 13,000° C.

minute. The area under the time versus temperature graph gives the amount of energy expended in heating the cells during the pasteurisation process. It has been found that a rapid heating and/or rapid cooling (which correspond to the first and third stages of the second aspect, respectively) can provide advantages, such as a better quality oil. In addition, the amount of energy required for the pasteurisation process can be reduced in comparison with pasteurisation processes described in the art. This third aspect therefore concerns to the energy input required for the pasteurisation process.

A fourth aspect of the invention relates to a process for pasteurising microbial cells, the process comprising (heating the cells and so) maintaining the cells at an elevated temperature (T, ° C.) for a time (t, minutes), for example at a plateau stage, wherein the product tT (that is to say the multiplication of the time and temperature parameters, for example during the plateau stage) is from 140 to 100,800° C. minute. As will be realised, this fourth aspect is similar to the second aspect, in that it contains a plateau stage. The cells here may be held at a constant or maximum temperature. The product tT can therefore represent the area under the time versus temperature graph for this plateau stage.

First Aspect—Rapid Heating

In this aspect the cells are heated so that the temperature of the cells passes through or from 40° C. to 70° C. (or 60° C.) in no more than 30 minutes (such as no more than 15 minutes). Preferably the time taken to pass through from 40 to 70° C. takes no more than 40 to 50 minutes. Alternatively or in addition the cells are heated at a rate of at least 0.5° C./minute. Of course, the microbial cells may start (or be heated) at a temperature below 40° C. For example, the cells may be at room or ambient temperature. The cells may be at fermentation temperature, such as 30°±5° C. Thus the cells may be at from 20 to 40° C., such as from 23 to 27° C. (or from 25 or 29 to 32 or 37° C.), when heating (pasteurisation) begins. In some cases the microbial cells may have been cooled, for example after fermentation has finished. Thus the cells may have a (starting) temperature of from 5 to 10° C., such as from 7 to 9° C., when heating begins.

The microbial cells may be heated so that their temperature rises above (60 or) 70° C. Thus, this may not be the final temperature of the microbial cells during pasteurisation. Indeed, the cells maybe heated to a temperature above (60 or) 70° C. The temperature may rise until a temperature of from 70 to 90, 110 or 130° C., such as from 75 to 87° C., and optimally from 78 to 84° C., is reached. The maximum temperature during pasteurisation may therefore be within these ranges, but for some embodiments may be up to 100, 120 or 140° C. Preferably, the cells are held or maintained at that (maximum) temperature.

Hence it will be realised that the cells can be heated at a temperature below, or starting from, 40° C., up to a temperature of 70° C. or higher. The 40 to 70° C. range may provide a 'snapshot' in broader heating/temperature range for which a time (and hence rate) can be specified (and hence calculated).

It will be calculated that the heating (of 40 to 70° C. in 30 minutes) is a rate of 1° C./minute. However, the rate can be slightly lower than this if necessary, and in the first aspect the rapid heating means a heating rate greater than 0.5° C./minute. Preferably, the rate is at least 0.6, 1.0, or even 1.5° C./minute. However, particularly fast heating rates are contemplated, depending on the equipment and the volume or weight of the microbial cells to be heated. Heating rates in excess of 2.0 or even 2.5° C./minute are thus within the invention.

Particularly high heating rates can be obtained using specialised equipment. This may reach a high temperature in a short period of time, and in doing so this may minimise any oxidation or damage to the PUFA or microbial oil that may be later isolated. Thus, heating may take place up to a maximum temperature of up to 140, 150 or even 160° C. Preferably, heating can be up to a temperature range within 100 to 180° C., such as 120 to 160° C., preferably from 130 to 150° C. Using particularly rapid heaters, these temperatures can be achieved particularly quickly, for example within a time less than one minute (30 seconds). Such temperatures could be reached within 20, 30, 40 or 50 seconds, or may take up to 150, 175, 200, 225 or 250 seconds. However, such temperatures can be reached in as little as 2, 4, 6, 8 or 10 seconds, for example if one is using an infusion heater, or with relatively small samples. Thus, heating rates of up to 50, 100, 150 or even 200° C. per minute are achievable. Slightly lower heating rates of 5 or 10 to 50 or 60° C. per minute are thus possible, such as from 15 to 45° C. per minute.

This rapid heating during rapid pasteurisation has been found not only to be more efficient, and requiring less energy, but it appears to be at least one factor responsible for obtaining a better quality microbial oil (once extracted from the cells following pasteurisation).

Second Aspect—Three Stage Pasteurisation Protocol

The first stage can be a heating stage. This, in effect, corresponds to the rapid heating described in the first aspect of the invention, and therefore all features and characteristics of the first aspect apply to the first (heating) stage of the second aspect *mutatis mutandis*.

The second stage is when the cells are at a plateau (in temperature). The cells can thus be held at a particular desired temperature (plus or minus 1 or 2, 5 or even 10° C.) for a desired length of time. The cells can thus be maintained at a constant temperature. Preferably this temperature (or range of temperatures), at the plateau stage, is the maximum temperature reached during the pasteurisation protocol. The temperature at the plateau stage (and/or the maximum temperature during pasteurisation) is preferably at least 70° C. It may be below 90 or 100° C., suitably from 70 to 85° C., such as from 70 to 77° C. Alternatively, it may be from 80-160° C., such as from 100-140° C.

The length of time of the plateau stage, or at which the cells are held at the desired or maximum temperature, can be from 5 seconds to 90 minutes, such as from 1 or 10 to 80 minutes, for example from 20 to 70 minutes. Optimally, this time is from 40 or 50 to 60 or 70 minutes, such as from 45 to 65 minutes, advantageously at from 55 to 63 minutes. Particularly short times, e.g. from 8 seconds to 5 minutes are also possible.

The third stage is a cooling stage. Preferably, the cells are cooled to a temperature which is the same as, or within, the ranges mentioned for the start of the heating (or first stage). Preferably, the microbial cells are cooled and/or heated linearly (in the first and/or third stages, as appropriate), that is to say when plotted on a time versus temperature graph the cooling or heating profile appears (approximately) as a straight line. The cells may be allowed to cool, or they may be actively cooled, for example using a heat exchanger and/or a cooling substance, for example (down) to ambient temperature or to room temperature, or lower.

Preferably the cooling rate is at least 0.4, 0.6, 1.0 or 1.5° C./minute. These values represent achievable cooling rates where the cells are allowed to cool. However, more rapid cooling rates are possible, especially if active cooling is employed. Thus, cooling rates of at least 2.0, 2.5, 3.0 or even 3.5° C./minute are attainable. However, higher cooling rates, such as above 5° C. per minute are possible, e.g. from 7 or 10 to 50 or 60° C. per minute, preferably from 15 to 45° C. per minute.

The preferred heating and/or or cooling rate is preferably maintained over at least 10, 20 or 30° C., although in some embodiments this can be achieved over at least a range of 40 or 50° C.

It will be realised that with a rapid heating stage and rapid cooling stage the amount of energy-used in pasteurisation can be reduced. Not only can this result in cost savings, but it may not adversely affect the quality of the (eventual) microbial oil, indeed it appears to have beneficial effects on the oil.

Third Aspect—Area Under Time Versus Temperature Graph (Energy Input)

From the second aspect it will be apparent that if the pasteurisation protocol of the invention is plotted on a time versus temperature graph, a trapezium shape is achieved. The first (heating) and third (cooling) stages may each be triangular in shape, while the middle or second (plateau) stage (the subject of the fourth aspect) is (usually) rectangular. The area under the time versus temperature graph represents the amount of energy inputted into the system. By splitting the pasteurisation protocol into three parts, one can calculate the area of the graph, and therefore the energy input.

In the third aspect, the area under the time (in minutes) versus temperature (in ° C.) graph is below 13,000° C. minute. However, amounts well below this have been achieved, and values below 11,000, 10,000, 9,000, 8,000 or even, 1,000 ° C. minute are possible. In preferred aspects of the invention, these values can be no more than 7,000, 6,000 or 800° C. minute. In the graph referred to, the time is plotted on the x axis (or the horizontal axis or abscissa) and 0° C. represents the origin. The temperature will thus be plotted on the y axis (or the vertical axis, or ordinate) and 0° C. represents the origin.

Once the microbial cells have been heated to their pasteurisation temperature, they can then cool (or are cooled). The cells are usually cooled to room or ambient temperature, or at least a temperature below 30° C. There is therefore a time not only for the cells to be heated from 30 to 60° C., but also a time for the cells to cool from 60° C. down to 30° C. One can sum these two times to provide a combined 30-60 to 30° C. heating and cooling time. Preferably, this combined only is less than 150 minutes, such as less than 120 or 100 minutes. However, with smaller samples, much faster times can be achieved, and the combined (30 to 60 and back down to 30° C.) time may be less than 70, 50 or even 30 minutes.

Fourth Aspect—Pasteurisation Protocol with Plateau Stage

This protocol can be one according to the second aspect, where there is a (e.g. first) heating stage, and a (e.g. second) cooling stage, the sandwiching a (e.g. second, or middle or intermediate) plateau stage. However, that is not essential, and other pasteurisation protocols can be envisaged. The fourth aspect relates to preferred features of this plateau stage. All features and characteristics of the second (and other) aspects apply to this fourth aspect *mutatis mutandis.*

The cells are maintained or held at a particular desired temperature (plus or minus 1, 2, 5 or even 10° C.) for a temperature (T, ° C.) for a time (t, minutes). These two parameters can be multiplied together to give the product tT. This is suitably from 140 or 280 to 50,000 or 100,800° C. minute. Preferably this product is from 500, 1,000, 2,000 or 3,000 or even 6,000 up to 10,000, 18,000 or 25,000° C. minute. Optimally, the product tT is from 2,000 to 6,000, such as from 3,000 to 5,000, optimally from 4,000 to 4,500° C. minute. In some embodiments, the product tT is from 13 to 900, such as from 100 or 200 to 700 or 800, optimally from 300 to 400 to 600 or 700° C. minute.

Thus in a similar manner to the third aspect, it will be realised that the product tT represents the area under the time versus temperature graph of the cells when maintained at the elevated temperature. Thus, the multiplication factor tT is, in effect, the area under the graph for just the plateau (but not heating or cooling) stage.

Extraction of a PUFA

A fifth aspect of the present invention relates to a process for obtaining a PUFA from microbial cells, the process comprising pasteurising the cells according to any of the first, second, third or fourth aspects of the invention, as previously described, and extracting and/or isolating a PUFA from the pasteurised cells.

A sixth aspect of the present invention relates to a microbial oil which may comprise at least 40% arachidonic acid (ARA) and/or may have a triglyceride content of at least 90%. The oil may have a POV of less than 2.5, 1.5, 0.8, 0.6 or even 0.5 and/or an AnV of less than 1.0. The oil is preparable by the process of the fifth aspect.

Polyunsaturated Fatty Acids (PUFAs) and Microbial Oils

The PUFA can either be a single PUFA or two or more different PUFAs. The or each PUFA can be of the n-3 or n-6 family. Preferably it is a C18, C20 or C22 PUFA. It may be a PUFA with at least 18 carbon atoms and/or at least 3 or 4 double bonds. The PUFA can be provided in the form of a free fatty acid, a salt, as a fatty acid ester (e.g. methyl or ethyl ester), as a phospholipid and/or in the form of a mono-, di- or triglyceride.

Suitable (n-3 and n-6) PUFAs include:
docosahexaenoic acid (DHA, 22:6 Ω3), suitably from algae or fungi, such as the (dinoflagellate) *Ciypthecodinium* or the (fungus) *Thraustochytrium;*
γ-linolenic acid (GLA, 18:3 Ω6);
α-linolenic acid (ALA, 18:3 Ω3);
conjugated linoleic acid (octadecadienoic acid, CLA);
dihomo-γ-linolenic acid (DGLA, 20:3 Ω6);
arachidonic acid (ARA, 20:4 Ω6); and
eicosapentaenoic acid (EPA, 20:5 Ω3).

Preferred PUFAs include arachidonic acid (ARA), docosohexaenoic acid (DHA), eicosapentaenoic acid (EPA) and/or γ-linoleic acid (GLA). In particular, ARA is preferred.

The PUFA may be produced by the cells pasteurised in the process of the invention, such as a microbial cell. This may be a bacteria, algae, fungus or yeast cell. Fungi are preferred, preferably of the order Mucorales, for example *Mortierella, Phycomyces, Blakeslea, Aspergillus, Thraustochytrium, Pythium* or *Entomophthora.* The preferred source of ARA is from *Mortierella alpina, Blakeslea trispora, Aspergillus terreus* or *Pythium insidiosum.* Algae can be dinoflagellate and/or include *Parphyridium, Nitszchia,* or *Crypthecodinium* (e.g. *Ctypthecodinium cohnii*). Yeasts include those of the genus *Pichia* or *Saccharomyces,* such as *Pichia ciferii,* Bacteria can be of the genus *Propionibacterium.* The microbial oil may be a liquid (at room temperature).

It is preferred that most of the PUFA is in the form of triglycerides. Thus, preferably at least 50%, such as at least 60%, or optimally at least 70%, of the PUFA is in triglyceride form. However, the amount of triglycerides may be higher, such as at least 85%, preferably at least 90%, optimally at least 95% or 98% of the oil. Of these triglycerides, preferably at least 40%, such as at least 50%, and optimally at least 60% of the PUFA is present at the α-position of the glycerol (present in the triglyceride backbone), also known at the 1 or 3 position. It is preferred that at least 20%, such as at least 30%, optimally at least 40% of the PUFA is at the β(2) position.

The microbial oil may comprise at least 10, 35, 40 or 45% or more of a desired PUFA, such as arachidonic acid. It can have triglyceride content of at least 90%. Preferably the microbial oil has a triglyceride content of from 90 to 100%, such as at least 96%, preferably at least 98%, more preferably at least 99% and optimally above 99.5%. Typically, the microbial oil will have an eicosapentaenoic acid (EPA) content of below 5%, preferably below 1% and more preferably below 0.5%. The oil may have less than 5%, less than 2%, less than 1% of each of $C_{20}$, $C_{20:3}$, $C_{22:0}$ and/or $c_{24:0}$ polyunsaturated fatty acid (PUFAs). The free fatty acid (HA) content may be ≤0.4, 0.2 or 0.1. The oil may have little or no GLA and/or DGLA.

The microbial oil may be a crude oil. It may have been extracted from the cells by using a solvent, such as supercritical carbon dioxide, hexane or isopropanol.

Pasteurisation Process

Pasteurisation will usually take place after fermentation has finished. In a preferred embodiment, pasteurisation will finish the fermentation, because the heat during pasteurisation will kill the cells, Pasteurisation may therefore be performed on the fermentation broth (or the cells in the liquid (aqueous) medium), although it can be perfolined on the microbial biomass obtained from the broth. In the former case, pasteurisation can take place while the microbial cells are still inside the fermenter. Pasteurisation preferably takes place before any further processing of the microbial cells, for example granulation (e.g. by extrusion) crumbling, or kneading.

Preferably the pasteurisation protocol is sufficient to inhibit or inactivate one or more enzymes that can adversely affect or degrade a PUFA or microbial oil, for example a lipase.

Once fermentation has been finished, the fermentation broth may be filtered, or otherwise treated to remove water or aqueous liquid. After water removal, one may obtain a biomass "cake". If pasteurisation has not taken place, then the dewatered cells (or biomass cake) can be subjected to pasteurisation.

PUFA Extraction Process

The PUFA (or microbial oil, usually comprising the PUFA) may then be extracted from the (pasteurised) microbial cells. Preferably, it is extracted from (e.g. dried) granules (e.g. extrudates) containing the cells. The extraction can be performed using a solvent. Preferably a non-polar solvent is used, for example a $C_{1-8}$, preferably $C_{2-6}$, alkane, for example hexane. One may use carbon dioxide (in a liquid form, for example in a super critical state).

Preferably, the solvent is allowed to percolate over the dried granules. Suitable micro-organism granulation and extrusion techniques and subsequent extraction of a microbial PUFA containing oil, are described in WO-A-97/37032.

The solvent allows one to obtain a crude PUFA containing oil. This oil can be used in that state, without further processing, or it can be subjected to one or more refining steps. However, a crude oil is usually one that contains a solvent, such as a solvent used to extract the oil (e.g. hexane, or an alcohol such as isopropyl alcohol) or that has not been subjected to one (or preferably all) of the following refining step. Suitable refining protocols are described in International patent application no. PCT/EP01/08902 (the contents of this document and all others described herein are hereby incorporated by reference). For example, the oil can be subjected to one or more refining steps which can include acid treatment or degumming, alkali treatment or free fatty acid removal, bleaching or pigment removal, filtration, winterisation (or cooling, for example to remove saturated triglycerides), deodorising (or removal of free fatty acids) and/or polishing (or removal of oil-insoluble substances). All these refining steps are described in greater detail in PCT/EP01/08902 and can be applied to the steps described in the present application *mutatis mutandis*.

The resulting oil is particularly suitable for nutritional purposes, and can be added to (human) foods or (animal) feedstuffs. Examples include milk, infant formula, health drinks, bread and animal feed.

Microbial Cells

The microbial cells (or micro-organisms) used in the present invention can be any of those described earlier especially in the section concerning PUFAs and microbial oils. They may comprise, or be able to produce, a PUFA or microbial oil, and suitably the PUFA oil may be extracted or isolated from the cells. They may be in filamentous form, like fungi or bacteria, or single cells like yeast, algae and bacteria. The cells may comprise micro-organisms that are yeast, fungi, bacteria or algae. Preferred fungi are of the order Mucorales for example, the fungus may be of the genus *Mortierella, Phycomyces, Blakeslea* or *Aspergillus*. Preferred fungi of the species *Mortierella alpina, Blakeslea trispora* and *Aspergillus terreits,*

As far as yeasts are concerned, these are preferably of the genus *Pichia* (such as of the species *Pichia ciferrii*) or *Saccharomyces*.

Bacteria can be of the genus *Propionibacterium*.

If the cells are from an algae, this is preferably a denoflagellate and/or belongs to the genus *Crypthecodiniuni*. Preferred algae of the species *Crypthecodinium cohnii*.

Heating

This can be performed by heating (the cells) directly or indirectly. The heating, if direct, may be by passing steam into the fermenter. An indirect method may use a medium via heat exchangers, either through the wall of the fermenter, or with heating coils, or an external heat exchanger such as a plate heat exchanger.

Usually, pasteurisation will take place in the fermenter vessel in which fermentation has occurred. However, for some organisms (such as bacteria) it is often preferred to remove the cells from the vessel first, and then pasteurise. Pasteurisation may take place before other processing of the organisms, for example drying or granulation.

Pasteurisation will usually kill most, or if not all, of the micro-organisms. Following pasteurisation, at least 95%, 96% or even 98% of the micro-organisms have been killed, that is to say they are not alive, Acidification In some cases it is desirable to reduce the risk of growth of the pasteurised cells. One possibility is to acidify the cells with a suitable acid. Thus, in order to prevent the outgrowth of microbial species, adjusting the cells to a pH range of 3 to 4 may be desirable. However, broader pH ranges can be employed depending on the cells, and so the pH may be adjusted from 2 to 5, optimally at a range of about 3.3 to 3.7.

Acidification of the cells may take place before pasteurisation. However, it is preferably conducted afterwards.

The pH can be adjusted by any suitable means, or by any suitable acid. Preferably this is achieved using phosphoric acid, such as 85%, or diluted 55% or 33% phosphoric acid.

Peroxide Value (POV)

Preferably the POV of the microbial oil is from 4 to 8 or 12, especially for a crude oil. However, the POV may be no more than 3.0, 2.5 or 2.0. However, much lower POV values can be obtained using the process of invention, and these values may be less than 1.5 or less than 1.0. Values less than 0.8 or 0.6 and even less than 0.4. POV can be obtained. Values (from embodiments) ranged from 1.3 (or 0.8) to 0.4. The unit (for POV) is usually meq/kg.

Anisidine Value (AnV)

This value can give a measure of the aldehyde content. Preferably the anisidine value of the microbial oil is from 5, 6, 7 or 10 to 15, 20 or 25, especially for a crude oil. Suitably the AnV no more than 20, for example no more than 15. It may be no more than 10 or even no more than 5. Preferably the POV and/or AnV values refer to a crude rather than refined, oil. AnV values (in preferred experiments) ranged from 15 to 5, optionally from 12 to 7.

Crude Versus Refined Oils

Some differences between these two oils are presented below. Each crude or refined oil may have one or more of the features in the following Table as for the crude or refined oil, as appropriate. A crude oil will usually contain an antioxidant (e.g. tocopherol, ascorbyl palmitate).

| Substance | Preferred (for crude) | Crude oil | Refined oil |
|---|---|---|---|
| Unsaponifiables | ≤3.5% (w/w) | 2.5% (w/w) | 1.8 (w/w) |
| Solvent (e.g. hexane) | <2000 ppm | 100-2000 ppm | Undetectable or ≤1 ppm |
| Phospholipids % | | 2-3.5 | 0.05 |
| Free fatty acids, as oleic | <1% | 0.2% | 0.08% |
| POV | ≤10 meq/kg | 6 meq/kg | 1.4 meq/kg |
| Non-solubles | <0.5% | 0.1% | — |
| Phosphorus | <1000 mg/kg | 5 mg/kg | — |
| Silicon | <500 ppm | 100 ppm | 24 ppm |
| Arsenic | <0.5 mg/kg | <0.04 mg/kg | <0.5 mg/kg |
| Cadmium | <0.2 mg/kg | <0.02 mg/kg | <0.1 mg/kg |
| Mercury | <0.04 mg/kg | <0.4 mg/kg | <0.04 mg/kg |
| Lead | <0.1 mg/kg | <0.1 mg/kg | <0.1 mg/kg |
| Copper | <0.2 mg/kg | <0.2 mg/kg | <0.02 mg/kg |
| Moisture and volatiles | <1.0% | 0.5 | <0.02% |
| Phosphatide (P/ppm) | | 50-100 | <10 |

Suitably, the crude oil in the present invention may have one or more of the following features:
 (a) an unsaponifiables content of from 2.0 to 3.5% (w/w);
 (b) a solvent (eg. hexane) content of from 10, 50 or 100 ppm up to 1000, 1500 or 2000 ppm;
 (c) a free fatty acid content of from 0.1 or 0.2% to 1%, eg. 0.2-0.6 or 0.3-0.5%;
 (d) a POV value of from 2, 3, 4 or 6 to 10;
 (e) a phosphorus content of at least 2, 3 or 5 mg/kg;
 (f) a silicon content of from 50 or 100 ppm to 500 ppm; and/or
 (g) a water content of less than 1% or from 0.5 to 1 or 2%.

Uses of Oils and PUFAs

A sixth aspect of the invention relates to a composition comprising the oil of the fifth aspect, and where appropriate are or more (additional) substances. The composition may be a foodstuff and/or a food supplement for animals or humans. In embodiments of the invention which are for human consumption the oils may be rendered suitable for human consumption, typically by refining or purification of the oil obtained from the microbes.

The composition may be an infant formula or (human) foodstuff. Here the composition of the formula may be adjusted so it has a similar amount of lipids or PUFAs to normal breast milk. This may involve blending the microbial oil of the invention with other oils in order to attain the appropriate composition.

The composition may be an animal or marine feed composition or supplement. Such feeds and supplements may be given to any farm animals, in particular sheep, cattle and poultry. In addition, the feeds or supplements may be given to farmed marine organisms such as fish and shell fish. The composition may thus include one or more feed substances or ingredients for such an animal.

The oil of the invention may be sold directly as oil and contained in appropriate packaging, typically one piece aluminium bottles internally coated with epoxy phenolic lacquer, and flushed with nitrogen. The oil may contain one or more antioxidants (e.g. tocopherol, vitamin E, palmitate) each for example at a concentration of from 50 to 800 ppm, such as 100 to 700 ppm.

Suitable compositions can include pharmaceutical or veterinary compositions, e.g. to be taken orally or cosmetic compositions. The oil may be taken as such, or it may be encapsulated, for example in a shell, and may thus be in the form of capsules. The shell or capsules may comprise gelatine and/or glycerol. The composition may contain other ingredients, for example flavourings (e.g. lemon or lime flavour) or a pharmaceutically or veterinary acceptable carrier or excipient.

Preferred features and characteristics of one aspect of the invention are applicable to another aspect *mutatis mutandis*.

The invention will now be described, by way of example with reference to the following Examples, which are provided by way of illustration and are not intended to limit the scope.

EXAMPLE 1

Oxidation during production of a microbial containing PUFA oil is thought to be caused by enzymatic activity. Pasteurisation was considered as a method of stabilising oxidation during processing of the microbial cells to obtain the microbial oil. The extent of the stabilisation was found to be dependent upon the pasteurisation conditions.

A number of experiments were therefore performed in order to determine which pasteurisation conditions could affect the level of oxidation, and in particular the peroxide value (POV) of the oil. Peroxide values were determined using the standard protocol detailed in AOCS:Cd8-53.

The experiments follow the following protocol: fermentation; storage; pasteurisation; (microbial oil) extraction; analysis of oil.

The fungus *Mortierella alpina* was cultivated in a fermenter. The fermentation lasted approximately 148 hours. M alpina produced the PUFA called arachidonic acid (ARA). The biomass was removed from the fomenter, and stored (at a temperature below −18° C.).

Samples of the *M. alpina* biomass were removed from the fermentation broth, while still resident, inside the fermenter, and frozen immediately.

Various pasteurisation protocols were tried. Pasteurisation was conducted at three different temperatures, namely 40, 70 and 85° C. The protocol followed a three stage process, with a first stage of rapid heating, followed by a plateau (a second or middle stage) at the desired temperature, which was the maximum temperature used. There was then a rapid cooling (third) stage. Different samples of the biomass were subjected to a middle (plateau) stage of three different times, namely one, two and 24 hours.

Following pasteurisation, the microbial oil was obtained using a wet extraction technique. This sample of biomass was filtered, squeezed (under pressure) and the oil extracted.

The microbial oil was then analysed, primarily for the peroxide value (POV) using an AOCS method. The ARA content for some of the samples was determined. Analyses showed that the microbial oil obtained had approximately 420 g ARA per kg.

Detailed Protocol: Fermentation and Sample Extraction

One liter of fermentation broth was removed from the fermenter vessel and filtered (Seitz two liter filter, F-FA10). The resulting cake was then washed with 600 ml of demineralised water. The wet cake was blow dried for one minute, and then squeezed (using a HAFICO™ apparatus, tincture press, C-OAO21, 300-400 Atm) at 400 bar. The wet extrudate was then used to extract a microbial oil with 500 ml of hexane (Merck) at room temperature (20 to 25° C.) for one hour using an Ultra Turrax™ machine. The hexane was then decanted. The remaining cake was then washed with 250 ml of fresh hexane (with stirring, for 30 minutes) at room temperature. The hexane was decanted and then added to the previously extracted hexane.

The extract was then filtered using a glass filter in combination with a GFA glass filter. The hexane was then evaporated, using a Rotavapor™ machine, from the clear extract at about 50° C. for about 15 minutes. The oil was then transferred into gas-tight cups, and each sample cup was then flushed with nitrogen for 30 seconds. The sample cup was then closed and stored at −18° C.

Pasteurisation Protocols

Three different protocols (A, B and C) were tested. Each was composed of three stages, a first heating stage, a second plateau stage (at a maximum temperature) and a third cooling stage. Table 1 below shows the protocols of the three pasteurisation profiles.

Figure 1:
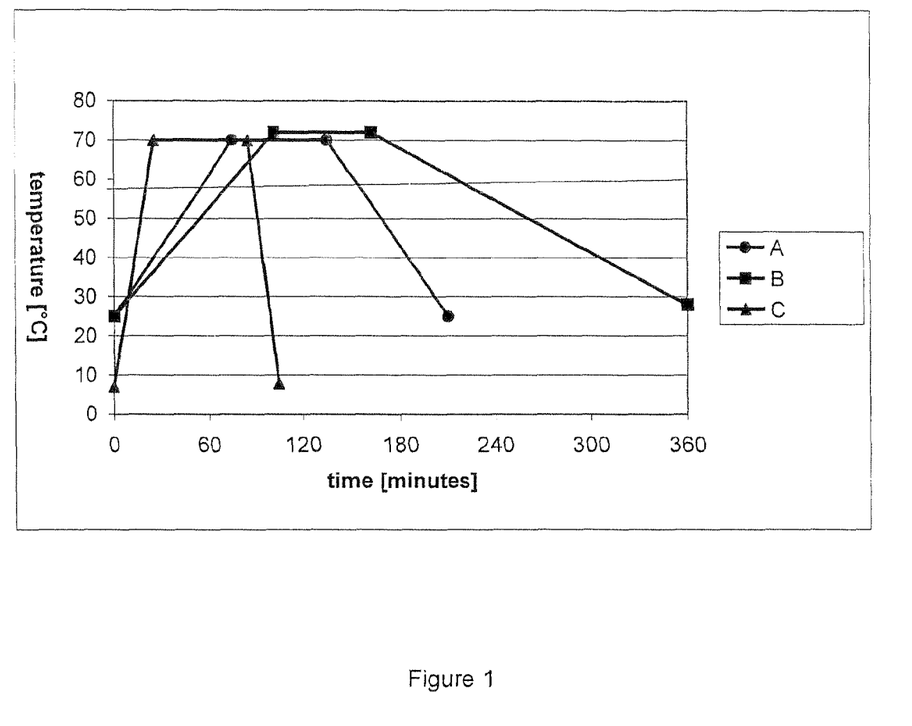
FIG. 1 is a graph of temperature (° C.) against time (minutes) for three pasteurisation protocols (A and C are within the invention, B is provided for comparison)

The three pasteurisation profiles A, B and C are additional shown graphically in FIG. 1. As realised, the area under the temperature (T, ° C.) versus time (t, minutes) graph can be calculated for each of the three steps in each profile, and then summed to give the total area under the graph for each of the three profiles. These calculations are additionally shown in Table 1 above.

The peroxide value (POV) was determined for the oils resulting from extraction from cells following the three pasteurisation protocols A, B and C. The POV of the extracted oils were 8.7, 14.3 and 2.4 respectively. Profile B had slow heating and slow cooling rates and is presented for comparison only. It gave the highest POV of 14.3.

By contrast, profiles A and C are both within the invention. Profile A has a faster heating and cooling rate in the first and third stages than, profile B. Preferably, in the invention, the heating and cooling rates are at least as fast as those shown in profile A. Profile A gave a POV of 8.7.

However, best results were obtained using profile C, which had a POV of only 2.4. As can be seen from FIG. 1, this had a very rapid heating stage, and fast cooling (third) stage.

EXAMPLE 2

Figure 2:
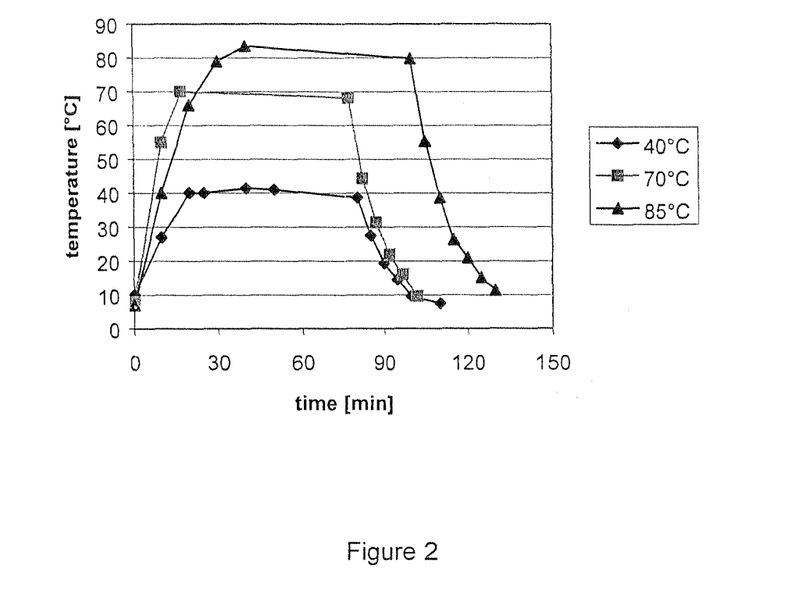
FIG. 2 is a graph of temperature (° C.) against time (minutes) for pasteurisation at three different temperature plateaus (40, 70 and 85° C.)

Experiments similar to Example 1 were conducted, except this time the temperature of pasteurisation was varied more widely, namely at 40° C. (for comparison), 70° C. and 85° C. The profile of temperature (° C.) vs. time (minutes) is shown in FIG. 2 and in Table 2 below. The profile was essentially the same for all samples, but of course with an extension of the pasteurisation plateau (from one hour to 4 or 24 hours) as appropriate.

TABLE 2

| 40° C. | | 70° C. | | 85° C. | |
|---|---|---|---|---|---|
| Time | temp | time | Temp | Time | temp |
| 0 | 10.0 | 0 | 8.0 | 0 | 7.0 |
| 10 | 27.0 | 10 | 55.0 | 10 | 40.0 |
| 20 | 40.1 | 17 | 70.0 | 20 | 66.0 |
| 25 | 40.0 | 77 | 68.2 | 30 | 79.0 |
| 40 | 41.4 | 82 | 44.3 | 40 | 83.5 |
| 50 | 41.0 | 87 | 31.3 | 100 | 79.8 |
| 80 | 38.7 | 92 | 21.8 | 105 | 55.3 |
| 85 | 27.5 | 97 | 16.0 | 110 | 38.7 |
| 90 | 19.3 | 102 | 9.7 | 115 | 26.3 |
| 95 | 14.5 | | | 120 | 21.0 |

TABLE 1

| | Time (t, minutes) | Temp (T, ° C.) at Time (t) | Stage | Temp change in stage (° C.) | Time per stage (mins) | Area under profile (° C. · min) | Heating/Cooling rate (° C./min) | Time to pass through 40-70° C. (min) | Combined 40-70-40° C. times (min) | Area under t versus T graph (° C. · min) |
|---|---|---|---|---|---|---|---|---|---|---|
| Profile A | 0 | 25 | | | | | | | | |
| | 75 | 70 | heat | 45 | t heat = 75 | 1687.5 | 0.6 | 50 | | 7575 |
| | 135 | 70 | pasteurise | 0 | t past = 60 | 4200 | 0 | | | |
| | 210 | 25 | cool | 45 | t cool = 75 | 1687.5 | 0.6 | 50 | 100 | |
| Profile B | 0 | 25 | | | | | | | | |
| (outside | 102 | 72 | heat | 48 | t heat = 102 | 4896 | 0.46 | 65.11 | | 13968 |
| invention for | 162 | 72 | pasteurise | 0 | t past = 60 | 4320 | 0 | | | |
| comparison) | 360 | 28 | cool | 48 | t cool = 198 | 4752 | 0.22 | 135 | 200.11 | |
| Profile C | 0 | 7 | | | | | | | | |
| | 25 | 70 | heat | 63 | t heat = 25 | 787.5 | 2.52 | 11.90 | | 5607.5 |
| | 85 | 70 | pasteurise | 0 | t past = 60 | 4200 | 0 | | | |
| | 105 | 8 | cool | 62 | t cool = 20 | 620 | 3.10 | 9.68 | 21.58 | |

TABLE 2-continued

| 40° C. | | 70° C. | | 85° C. | |
|---|---|---|---|---|---|
| Time | temp | time | Temp | Time | temp |
| 100 | 9.7 | | | 125 | 15.2 |
| 110 | 7.5 | | | 130 | 11.3 |

Samples from two different fermentations (both of Malpina), of different length, were tested. Sample nos. 11 to 20. Table 3 had a slightly longer fermentation where about 2 m³ of broth was transferred to an inoculum fermenter and the fermentation extended for 48 hours without any further addition of glucose.

After pasteurisation, the samples were processed, starting with filtration at a pressure of about 1 bar of nitrogen. The resulting cake was then washed with process water (about 0.6 of the initial broth volume). De-watering was accomplished using a fruit press at 300 to 400 bar piston pressure. Then, 500 ml of fresh hexane was added, and mixed for one minute using an Ultra-turrax machine for one minute. Extraction then took place for about one hour at ambient temperature. Following filtration, the resulting cake was washed With 250 ml of fresh hexane, and the resulting solvent was evaporated under vacuum at 60 to 70° C. It was then flushed with nitrogen and stored at −18° C.

Figure 3:
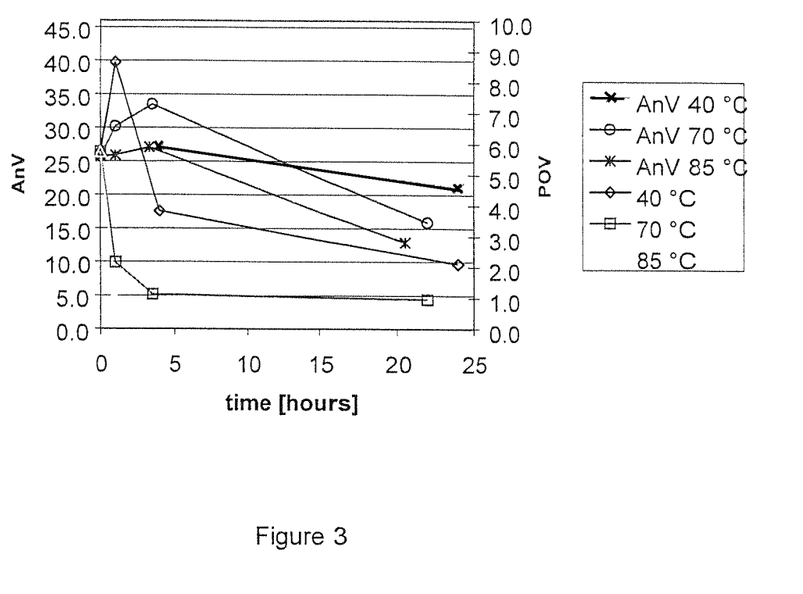
FIG. 3 is a graph of POV against time (hours)
Figure 4:
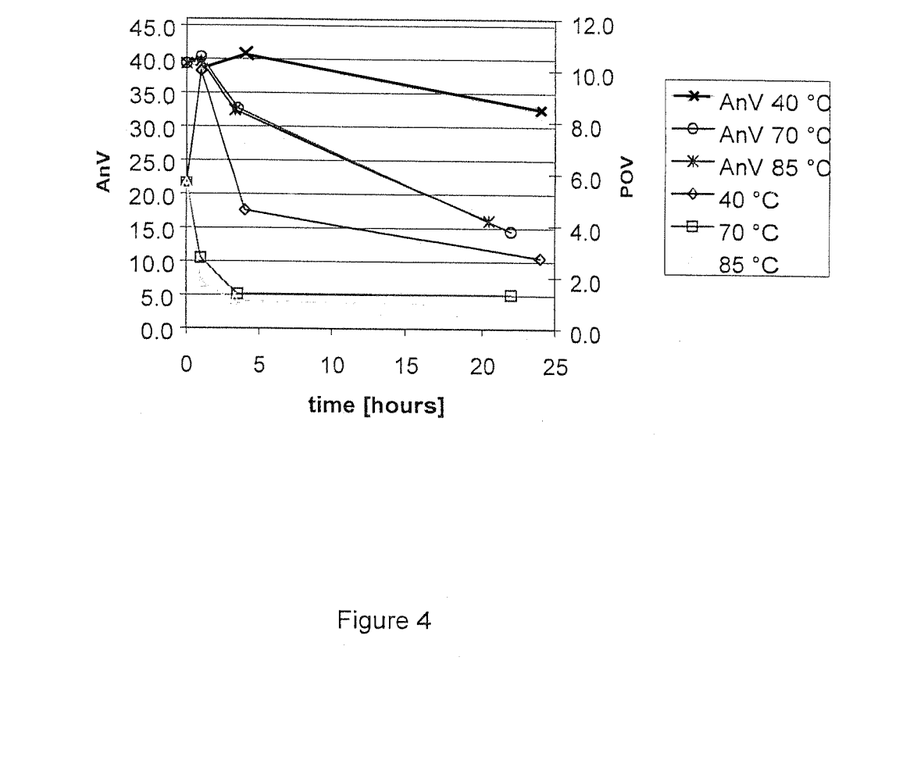

The results are shown in Table 3, which includes the first and second measured peroxide values, and an average of these two values, as well as the anisidine value (AnV). The reduction in POV and AnV are also shown in FIGS. 3 and 4 (for the shorter and longer fermentations, respectively).

TABLE 3

| Sample No. | $T_{past}$ (° C.) | $t_{past}$ (hrs) | POV1 | POV2 | $POV_{ave}$ | AnV |
|---|---|---|---|---|---|---|
| 1 | — | 0 | 6.0 | 5.4 | 5.7 | 25.7 |
| 2 | 40 | 1 | 8.8 | 8.5 | 8.6 | 25.9 |
| 3 | 40 | 4 | 3.8 | 3.8 | 3.8 | 27.1 |
| 4 | 40 | 24 | 2.1 | 2.2 | 2.1 | 21.0 |
| 5 | 70 | 1 | 2.2 | | 2.2 | 30.2 |
| 6 | 70 | 3.5 | 1.1 | 1.1 | 1.1 | 33.5 |
| 7 | 70 | 22 | 0.7 | 0.7 | 1.0 | 15.9 |
| 8 | 85 | 1 | 1.2 | 1.2 | 1.2 | 25.9 |
| 9 | 85 | 3.3 | 0.7 | 0.8 | 0.7 | 27.1 |
| 10 | 85 | 20.5 | 0.5 | 0.5 | 0.5 | 12.9 |
| 11 | — | 0 | 5.9 | 5.4 | 5.6 | 39.3 |
| 12 | 40 | 1 | 9.9 | 10.1 | 10.0 | 38.7 |
| 13 | 40 | 4 | 4.8 | 4.5 | 4.6 | 40.7 |
| 14 | 40 | 24 | 2.5 | 3.0 | 2.8 | 32.3 |
| 15 | 70 | 1 | 2.7 | 2.8 | 2.7 | 40.3 |
| 16 | 70 | 3.5 | 1.6 | 1.7 | 1.3 | 32.7 |
| 17 | 70 | 22 | 1.0 | 0.9 | 1.3 | 14.5 |
| 18 | 85 | 1 | 1.8 | 1.8 | 1.8 | 39.7 |
| 19 | 85 | 3.3 | 1.1 | 1.1 | 1.1 | 32.4 |
| 20 | 85 | 20.5 | 0.9 | 1.0 | 0.9 | 16.1 |

From the results it will be seen that with no pasteurisation, the POV was 5.6 or 5.7. Pasteurisation at 40° C. did reduce the POV, but a relatively long time (such as 24 hours) at the pasteurisation temperature was required in order to reduce the POV to an acceptable value of 2.1.

Higher temperatures were considerably more successful. For example, pasteurisation for only 1 hour at 70° C. gave a POV of 2.2, when compared to a POV of 2.1 for 24 hours at 40° C. Even better values were obtained at higher temperatures, with 85° C. for 1 hour giving a POV value of only 1.2. (These figures are quoted for the shorter fermentation, although similar results can be found with cells grown in the longer fermentation).

FIGS. 3 and 4 thus show graphically how the POV and AnV values change with respect to different pasteurisation times. As expected, longer pasteurisation times give lower AnV and POV values. However, of more importance is the use of relatively high temperatures during pasteurisation. A marked decrease in AnV and POV was found when the pasteurisation temperature ($T_{past}$) was increased to 70° C., and even lower values were found at 85° C. (The top three lines, indicated by crosses, filled circles and asterisks show the AnV values, while the lower three lines, indicated by diamonds, squares and triangles, give the POV values).

Table 4 below shows the calculated product tT (in ° C. minute) for the nine different pasteurisation protocols (three different plateau temperatures and for three different times). This product in effect represents the area under the graph (of time, t, minutes vs. temperature, T, ° C.) for the plateau stage (after the heating stage but before the cooling stage).

TABLE 4

| | Temp (T, ° C.) | | |
|---|---|---|---|
| Time (t, hrs/mins) | 40 | 70 | 85 |
| 1 (60) | 2,400 | 4,200 | 5,100 |
| 4 (240) | 9,600 | 16,800 | 20,400 |
| 24 (1440) | 57,600 | 100,800 | 122,400 |

EXAMPLE 3

Further pasteurisation trials were conducted using fermentation broth, following fermentation on a production scale, using the fungus M. alpina, as previously exemplified. Unpasteurised broth (800 liters) was transported, and stored at 4° C. The broth was then transferred to a stirred vessel of 700 liters and 10 different pasteurisation protocols performed.

Firstly, pasteurisation was conducted at five different (maximum) temperatures, namely 140, 120, 100, 80 and 60° C. with a residence (plateau) time (at maximum temperature) of 8 seconds. Secondly, pasteurisation was conducted at 140, 120, 100, 80 and 60° C. with a resident (plateau) time *at maximum temperature of 300 seconds.

Samples (2 liters) were taken and then frozen directly at −18° C. Sterile samples (200 ml) were taken and frozen, and crude ARA oil recovered from the samples using the following protocol.

A sample of fermentation broth (1.7 liters) was filtered at 1 bar of $N_2$. The cake was washed with 0.6 volumes of condensed water, and squeezed for about 5 minutes at 400 $kg/cm^2$. Then, n-hexane (500 ml) was added to the wet cake, and crumbled using an Ultra Turrax machine at 24,000 rpm. The oil was extracted at ambient temperature (about 21° C.) over about 110 minutes. The suspension was filtered with a vacuum using a GF/A Whatman filter medium. The cake was washed with 250 ml of fresh hexane. The hexane was evaporated for 15 minutes in a water bath, having a temperature of about 60 to 70° C. The resulting oil was then transferred to gas-tight sample cups, which were flushed with nitrogen for 30 seconds, and then closed and stored prior to analysis at −18° C.

Figure 5:
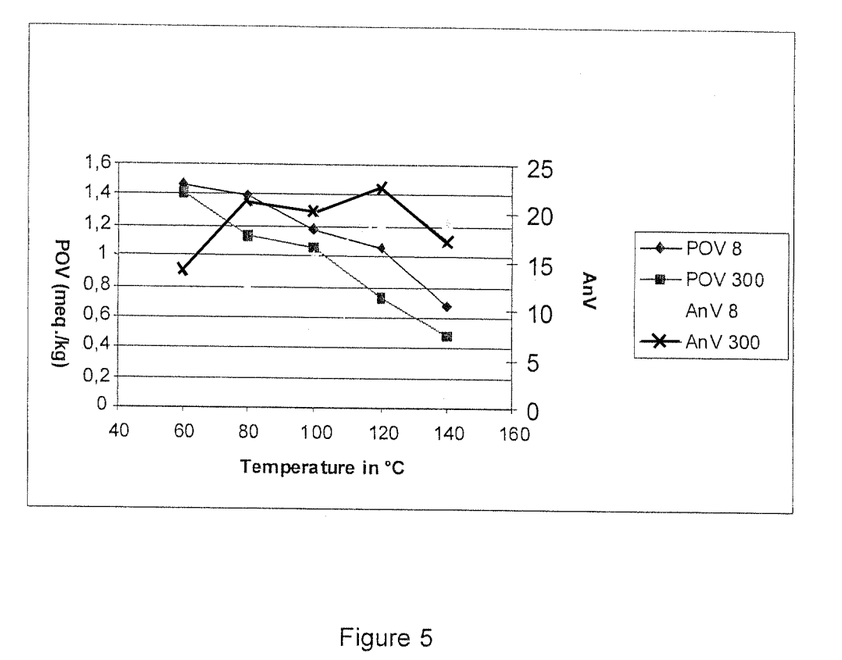
FIG. 5 is a graph of POV (meq/kg) and AnV against temperature (° C.) for pasteurisation at two different (residence/plateau) times (8 and 300 seconds)
Figure 6:
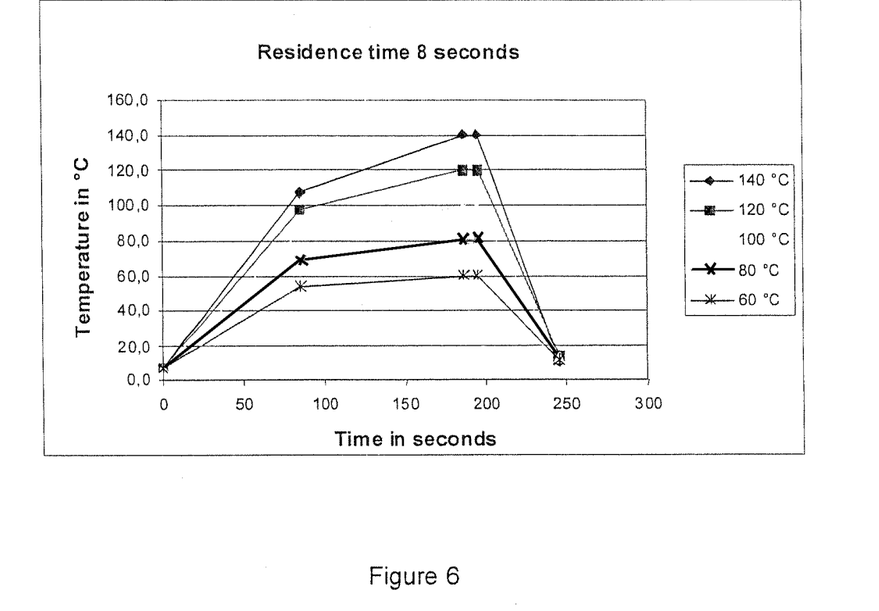
FIGS. 6 and 7 are graphs of temperature (° C.) against time (seconds) for two different (residence/plateau) time (8 seconds for FIG. 6, 5 minutes for FIG. 7) at five different temperatures (60, 80, 100 120 and 140° C.).
Figure 7:
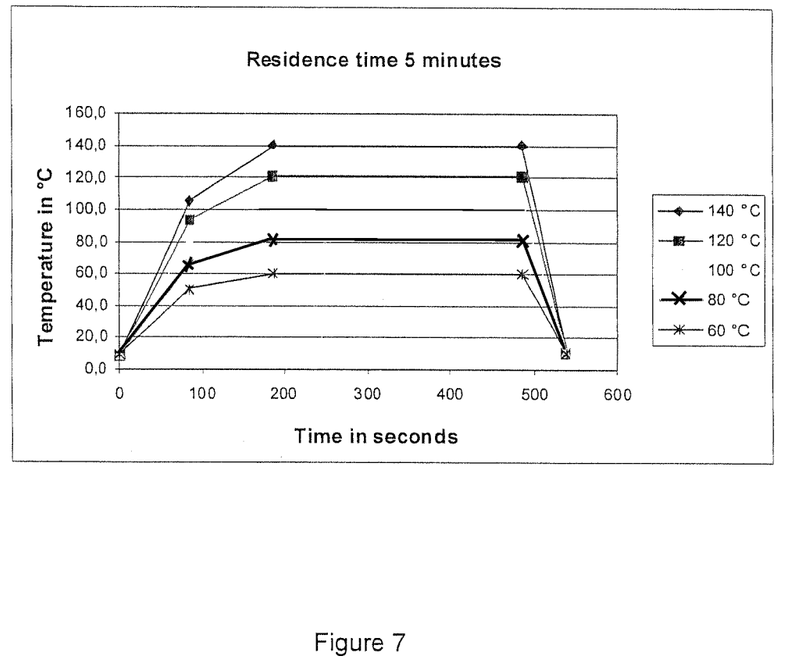

FIGS. 5, 6 and 7 provide the data following analysis. FIGS. 6 and 7 show the time against temperature profiles for the two sets of experiments, firstly of the plateau (residence) time of 8 seconds, and secondly for the plateau (residence) time of 5 minutes, at each of the 5 temperature settings, respectively. As will be seen from the graphs, the horizontal middle line (representing 8 seconds or 5 minutes) shows the plateau stage.

FIG. 5 shows the resulting POV and AnV values for all 10 of pasteurisation regimes As will be seen, lower POV values were obtained with increasingly higher temperatures, and the longer residence time (5 minutes) gave the lowest POV value.

The invention claimed is:

1. A process for obtaining an oil comprising docosahexaenoic acid (DHA) from microbial cells, the process comprising
(a) a process for pasteurizing the microbial cells, which comprises heating the cells and so maintaining the cells at an elevated temperature at a plateau stage wherein the temperature at the plateau stage is above 100 °C.; and (b) extracting or isolating the oil from the pasteurized cells.

2. A process according to claim 1, wherein the temperature at the plateau stage is above 110 °C.

3. A process according to claim 1, wherein the temperature at the plateau stage is from 100-160° C.

4. A process according to claim 3, wherein the temperature at the plateau stage is from 110-160 °C.

5. A process according to claim 3, wherein the temperature range at the plateau stage is from 100-140° C.

6. A process according to claim 1, wherein (a) comprises maintaining the cells at an elevated temperature (T, °C.) for a time (t, minutes) at a plateau stage wherein the product tT is from 140 to 100,800 °C. minute.

7. A process according to claim 1, wherein the oil comprises at least 10% DHA.

8. A process according to claim 7, wherein the oil comprises at least 35% DHA.

9. A process according to claim 1, wherein (b) comprises extracting the oil from the pasteurized microbial cells using a solvent.

10. A process according to claim 1, wherein (b) comprises extracting a crude DHA-containing oil from the pasteurized cells and subjecting the crude oil to one or more refining steps.

11. A process according to claim 1, which further comprises incorporating the oil in a foodstuff, food supplement, or infant formula.

12. A process according to claim 1, which further comprises blending the oil with another oil.

13. A process according to claim 1, wherein the cells comprise a yeast, a bacteria, an algae and/or a fungi.

14. A process according to claim 1, wherein the cells comprise a dinoflagellate.

15. A process according to claim 1, wherein the cells comprise a *Crypthecodinium*.

16. A process according to claim 1, wherein the cells comprise a *Thraustochytrium*.

17. A process for obtaining an oil comprising at least 35% docosahexaenoic acid (DHA) from microbial cells, the process comprising (a) a process for pasteurizing the microbial cells, which comprises heating the cells and so maintaining the cells at an elevated temperature at a plateau stage wherein the temperature at the plateau stage is above 80 °C.; and (b) extracting or isolating the oil from the pasteurized cells.

18. A process according to claim 17, wherein the temperature at the plateau stage is above 100 °C.

19. A process according to claim 18, wherein the temperature at the plateau stage is above 110 °C.

20. A process according to claim 17, wherein the temperature at the plateau stage is from 80-160 °C.

21. A process according to claim 20, wherein the temperature at the plateau stage is from 100-160 °C.

22. A process according to claim 21, wherein the temperature at the plateau stage is from 110-160 °C.

23. A process according to claim 21, wherein the temperature at the plateau stage is from 100-140 °C.

24. A process according to claim 17, wherein (a) comprises maintaining the cells at an elevated temperature (T, °C.) for a time (t, minutes) at a plateau stage wherein the product tT is from 140 to 100,800 °C. minute.

25. A process according to claim 17, wherein the cells comprise a yeast, a bacteria, an algae and/or a fungi.

26. A process according to claim 17, wherein the cells comprise a dinoflagellate.

27. A process according to claim 17, wherein the cells comprise a *Crypthecodinium*.

28. A process according to claim 17, wherein the cells comprise a *Thraustochytrium*.

29. A process according to claim 17, wherein the oil comprises at least 40% DHA.

30. A process according to claim 17, wherein (b) comprises extracting the oil from the pasteurized microbial cells using a solvent.

31. A process according to claim 30, wherein (b) comprises extracting a crude DHA-containing oil from the pasteurized cells and subjecting the crude oil to one or more refining steps.

32. A process according to claim 17, which further comprises incorporating the oil in a foodstuff, food supplement or infant formula.

33. A process according to claim 17, which further comprises blending the refined oil with another oil.

* * * * *